United States Patent
Krauskopf et al.

(10) Patent No.: US 7,358,277 B2
(45) Date of Patent: Apr. 15, 2008

(54) USE OF A LACTATE SALT FOR THE TREATMENT AND PROPHYLAXIS OF ATHEROSCLEROSIS

(75) Inventors: Jobst Krauskopf, Barum (DE); Erich Eistner, Gröbenzell (DE)

(73) Assignee: S.K. Enterprise GmbH, Hamburg (DE)

( * ) Notice: Subject to any disclaimer, the term of this patent is extended or adjusted under 35 U.S.C. 154(b) by 127 days.

(21) Appl. No.: 10/484,476

(22) PCT Filed: Jul. 22, 2002

(86) PCT No.: PCT/EP02/08153

§ 371 (c)(1),
(2), (4) Date: Jun. 29, 2004

(87) PCT Pub. No.: WO03/011263

PCT Pub. Date: Feb. 13, 2003

(65) Prior Publication Data

US 2004/0214892 A1    Oct. 28, 2004

(30) Foreign Application Priority Data

Jul. 20, 2001 (DE) ............................. 101 35 494

(51) Int. Cl.
*A61K 31/19* (2006.01)
(52) U.S. Cl. .................................................. 514/557
(58) Field of Classification Search ............... None
See application file for complete search history.

(56) References Cited

U.S. PATENT DOCUMENTS

| | | | |
|---|---|---|---|
| 3,125,494 A * | 3/1964 | Snell et al. ............... 435/139 |
| 4,412,986 A | 11/1983 | Kawata et al. | |
| 4,812,303 A * | 3/1989 | Iorio ......................... 424/44 |
| 5,262,153 A * | 11/1993 | Mishima et al. ........... 424/62 |
| 5,985,335 A * | 11/1999 | Dietl ........................ 424/610 |
| 6,042,849 A | 3/2000 | Richardson et al. | |
| 6,310,051 B1 * | 10/2001 | Karlsson et al. .......... 514/85 |
| 6,482,853 B1 * | 11/2002 | Brooks ...................... 514/513 |
| 2002/0170080 A1 * | 11/2002 | Farese et al. ............... 800/14 |

FOREIGN PATENT DOCUMENTS

| | | |
|---|---|---|
| DE | 296 23 285 U1 | 3/1998 |
| DE | 198 54 749 A1 | 5/2000 |
| DE | 100 08 880 A1 | 8/2000 |
| EP | 0 143 949 A1 * | 6/1985 |
| EP | 0 274 404 | 7/1988 |
| WO | WO 99 65337 A | 12/1999 |
| WO | WO 00 67750 A | 11/2000 |

OTHER PUBLICATIONS

Jones et al., The American Journal of Cardiology, vol. 81, Mar. 1, 1998, pp. 582-587 "The Curves Study".*
Harrison's Principles of Internal Medicine, 13th edition, vol. 1, pp. 1108-1116, (1994).*
The Merck Manual of Diagnosis and Therapy, 14th edition, Berkow et al. (eds.), published 1982 by Merck, Sharpe & Dohme, (NJ), pp. 386-389 and 550-555.*
The Merck Index, 11th edition, published 1989 by Merck & Co., Inc., p. 891, citation No. 5529.*
Patent Abstracts of Japan, vol. 016, No. 431, Sep. 9, 1992 (JP 04 148651A).
Database CA Online, Chemical Abstracts Service, Columbus, Ohio; Hagiwara, Satoshi, "Treatment for osteoporosis", AN 127:12760, 1996.
Database CA Online, Chemical Abstracts Service, Columbus, Ohio; Wang, C., "Milk tea with VA, VD and calcium lactate", AN 2000-476630 [42], 2000.
Database OPI, Section Ch, Week 200110 Derwent Publication Ltd., London, Class B04, Mar. 19, 1997, AN 2001-081199 [10].
Database WPI, Section Ch, Week 199729 Derwent Publication Ltd., London, Class B05, Jul. 5, 1997, AN 1997-311237 [29].
Database WPI, Section Ch, Week 200132 Derwent Publication Ltd., London, Class B04, Feb. 7, 2001, AN 2001-300860[32].

* cited by examiner

*Primary Examiner*—Raymond J. Henley, III
(74) *Attorney, Agent, or Firm*—Scully, Scott, Murphy & Presser, P.C.

(57) ABSTRACT

The use of a lactate metal salt, in particular an L-lactate, for the treatment of atheroscloerosis and/or for the prophylaxis or treatment of diseases caused by atherosclerosis is disclosed.

13 Claims, No Drawings

USE OF A LACTATE SALT FOR THE TREATMENT AND PROPHYLAXIS OF ATHEROSCLEROSIS

FIELD OF THE INVENTION

The present invention relates to the use of a lactate metal salt for the treatment and prophylaxis of atherosclerosis.

BACKGROUND OF THE INVENTION

Atherosclerosis, colloquially called arterial calcification, is one of the most serious and most frequent diseases in the Western world. Until now, it has not been possible to fully clarify its aetiopathogenesis. For example, numerous exogenous and endogenous noxae and diseases are held responsible for triggering or promoting atherosclerosis. Examples hereof are hypertonia, hyperlipidaemia, hyperfibrinogenaemia, diabetes mellitus, toxins, nicotine, antigen-antibody complexes, inflammation, etc. An increased lipid level in the blood; especially hypercholesterolaemia, i.e. raised cholesterol levels in the blood (>200 mg/dl), is without doubt a significant risk factor. One meaningful approach to the prophylaxis and, to a certain extent, therapy of this disease and its consequences (cardiac infarction, cerebral and peripheral circulatory disturbance, etc.) has so far been to bring down raised plasma lipid levels, especially raised plasma cholesterol levels.

Like other arteries, the coronary artery and especially the major coronary arterial branches may be affected by atherosclerosis. Coronary sclerosis which results in stenosis of the coronary flow canal or which, through the additional formation of thrombi, may cause partial or complete occlusion of the branches of the coronary artery is the most important cause of coronary heart disease. Proven risk factors are: smoking, excess weight, hypertonia, hyperlipoproteinaemia and diabetes mellitus. These factors must be taken into account for prophylaxis.

Plasma lipids are neutral fats, phospholipidos, cholesterol, cholesterol esters and free fatty acids. Since lipids are insoluble in water, they are transported in the blood not in free form, but rather in the form of so-called lipoproteins, i.e. bound to carrier proteins. The lipoproteins are subdivided into chylomicrons very low-density lipoproteins (VLDL), low-density lipoproteins (LDL), intermediate-density lipoproteins (IDL) and high-density with pyruvate should eliminate this irritating and toxic potential of these activated blood cells.

In another embodiment, the metal salt of the lactate is used as an alkali metal salt or alkaline earth metal salt of the lactate, preferably as calcium lactate. Calcium is capable thereby of binding the bile acids which have entered the intestine via the enterohepatic cycle. This reduces re-transport to the liver. In order to maintain the balance in the enterohepatic cycle, a greater amount of cholesterol must be converted in the liver to bile acid. This results in a decrease of the plasma cholesterol level. Not only does this have an impact on the generation of sclerotic arteries, but it also at the same time removes a possible main cause of artherosclerosis from the body, which further decreases the risk of atherosclerosis.

Calcium constitutes an important nutrient for normal growth and development. It helps in regulating the cell function and is an indispensable structural component of the bone. Since the body is not capable of producing calcium itself, it must be taken up through food. About 25 to 35% of the calcium taken up through food is absorbed in the intestine, mostly in the duodenum and in the jejunum, the remaining 65 to 75% of the calcium supplied are not used and thus excreted. Therefore, approximately two thirds to three fourths of the calcium supply are available for binding the bile acids and thus for the reducing the cholesterol level. On the other hand, the absorbed amount helps to improve the skeleton and thus to prevent osteoporosis.

Calcium lactate is characterised by good solubility. This permits improved calcium absorption, which increases the positive effect on the skeleton. Thereby, the absolute amount of calcium available in the intestine is reduced, this can, however, be easily counteracted by increasing the amount uptaken. Moreover, the amount of calcium in the human body is continuously subject to equilibration by means of absorption and secretion. The increased amount of calcium taken up is thus excreted for the most part and can possibly further increase, from the inside, the binding and, thus, secretion of bile acids.

In another embodiment according to the invention, a micro-encapsulation of the lactate metal salt or of a pharmaceutical composition made therefrom has proven to be especially advantageous. The micro-encapsulation can, for example, be carried out as described in the laid-open patent specifications DE 193 54 749 A1 and DE 100 08 880 A1 as well as in the German utility model DE 296 23 285 U1. In this process, the lactate salt is, for example, firmly enclosed in a capsule of a polysaccharide such as, e.g., alginate. In order to ensure that the capsule, which may be indigestible, does not prevent release of the lactate, which would make physiological utilisation by the organism impossible, a lipoproteins (HDL). Whilst the main component of LDLs is cholesterol, the HDLs have an especially high protein content and a comparatively low cholesterol content HDLs are able to take up cholesterol deposited on vessel walls and to pass it on to the IDLs.

Chylomicrons are produced during fat resorption in the intestinal wall they then come into the blood via the lymph and, after cleavage of the triglycerides by the lipoprotein lipase, release the so-called clearing factor, fatty acids, to fat tissues (for storage) and to the muscles (as a fuel). The remnants, which have a high cholesterol ester content, are now bound to a special receptor (remnant receptor) that is found only in liver cells, and are transported into the liver cell by this receptor. The cholesterol received by the liver cell is, on the one hand, converted to bile acids, which are then released into the intestine with the bile, and, on the other hand, is transported back into the circulation together with apoproteins, phospholipids and triglycerides in the form of VLDL.

The object of the present invention is to provide a pharmaceutical composition suitable for the treatment and/or prophylaxis of atherosclerosis and/or the prophylaxis or treatment of diseases caused by atherosclerosis.

DESCRIPTION OF THE INVENTION

It has surprisingly been found that the administration of a lactate metal salt results in a reduction of atherosclerosis.

Lactate is the salt of lactic acid and exists in the L-(+) form (dextrorotatory), the D-(–) form, and the DL form (racemate). The use of the L-form has proven to be especially advantageous.

Following intensive and detailed studies, the inventors have made the discovery that lactate dehydrogenase is released by damaged endothelial cells in the immediate vicinity of atherosclerotic events in the blood vessels, as a result of which lactate may be converted to pyruvate.

Pyruvate as an α-keto acid is capable of reacting with specific peroxides, by means of which these toxic compounds are removed from the reactive platform and thus from the atherosclerotic mechanism. It is now possible, by the administration of lactate as a metal salt, to suppress this mechanism to a greater extent and to reduce the risk of atherosclerosis or, in the best possible case, to suppress it completely.

The same is true for inflammatory sites: the formation of hypochlorite from chloride and hydrogen peroxide by the myeloperoxidase reaction of activated neutrophilic granulocytes is a route which damages and irritates the tissue. Likewise, the ionic reaction of peroxide digestible component, such as e.g. starch, can be added to the capsule. By a skilful selection and/or combination of the soluble and insoluble components of the capsule, it is thus possible to targetedly control the release of the micro-encapsulated lactate salt in various areas of the digestive tract. Gradual release of the lactate in the intestine, for example a release of 50 to 80 wt. %, preferably 60 to 70 wt. %, and especially 62.5 wt. % of the lactate in the small intestine and a release of 20 to 50 wt. %, preferably 30 to 40 wt. %, especially 62.5 wt. % of the lactate in the large intestine is one possibility of targeted release. Another advantageous effect can be achieved due to an extended stability provided by protecting the encapsulated composition against, for example, environmental influence.

The dosage of the metal salt of the lactate is preferably such that the daily dose is between 2.0 g and 6.0 g, preferably between 3.0 g and 5.0 g, most preferably about 4.0 g of lactate. The daily dose in the form of calcium lactate is usually 2.5 g to 7.0 g, preferably between 4.0 g and 6.0 g, most preferably 5.0 g.

Administration advantageously takes place in on to six daily dosages, a daily dosage of four to six times being preferred. The actual dosage interval and the amount of the dosage depend, however, on factors such as age, weight and/or gender, which may vary from person to person. An increased uptake of the lactate is particularly advantageous for pregnant women or breast-feeding mothers. An additional advantageous effect can, for example, be achieved by taking the preparation immediately before or during a meal. When administering the lactate salt to mammals in general, the dosage occurs likewise dependent on the animal species and weight. The metal salt of the lactate can be included in a composition for administration to a subject, where the composition can take a solid form as a lozenge, powder or granulate, or a liquid form as a syrup or juice.

According to the invention, the lactate metal salt can be used for the preparation of food, such as dietetic food products and/or food supplements, whereby these obtain a property enabling a reduction of the atherosclerosis risk when administered orally. In the form of calcium lactate, it is additionally possible to lower the cholesterol levels. Examples of such food products are milk products or fruit juices enriched with the lactate.

The lactate salt may also be used for the prophylaxis and/or treatment of diseases such as osteoporosis, hypertonia and inflammatory processes such as arthritis etc. in mammals and especially humans. The prophylaxis and/or treatment of coronary heart diseases is preferred.

The invention claimed is:

1. A method for the treatment of atherosclerosis or diseases caused by atherosclerosis in a subject, comprising administering to the subject a pharmaceutical composition comprising calcium lactate, wherein calcium lactate is present as the only effective anti-atherosclerosis agent and the only effective agent against diseases caused by atherosclerosis.

2. A method for the treatment of atherosclerosis in a subject, comprising administering to the subject a pharmaceutical composition comprising calcium lactate, wherein calcium lactate is present as the only effective anti-atherosclerosis agent.

3. A method for the treatment of diseases caused by atherosclerosis in a subject comprising administering to the subject a pharmaceutical composition comprising calcium lactate, wherein calcium lactate is present as the only effective agent against diseases caused by atherosclerosis.

4. The method according to any one of claims 1 or 2-3, wherein the lactate is L-lactate.

5. The method according to any one of claims 1 or 2-3, wherein the composition is micro-encapsulated.

6. The method according to any one of claims 1 or 2-3, wherein the composition is for oral administration.

7. The method according to any one of claims 1 or 2-3, wherein the composition is administered at a daily dose of between 2.0 g and 6.0 g of lactate.

8. The method according to claim 1 or claim 3, wherein the diseases caused by atherosclerosis are coronary heart diseases.

9. The method according to any one of claims 1 or 2-3, wherein the composition further contains additives suitable for preparing food, especially dietetic food or food supplements.

10. The method according to any one of claims 1 or 2-3, wherein the composition further comprises pharmaceutically acceptable additives and/or corners.

11. The method according to any one of claims 1 or 2-3, wherein the composition is present in solid farm as a lozenge, powder or granulate or in liquid form as a syrup or juice.

12. The method according to any one of claims 1 or 2-3, wherein the daily dose is between 3.0 g and 5.0 g of lactate.

13. The method according to any one of claims 1 or 2-3, wherein the daily dose is 4.0 of lactate.

* * * * *